United States Patent [19]

Mason et al.

[11] Patent Number: 4,643,176

[45] Date of Patent: Feb. 17, 1987

[54] ATHLETIC KNEE PROTECTOR WITH BOWED LEAF SPRING STRUCTURE

[75] Inventors: Bradley R. Mason, Carlsbad; Jeffrey T. Mason, Escondido, both of Calif.

[73] Assignee: Don Joy, Inc., Carlsbad, Calif.

[21] Appl. No.: 756,660

[22] Filed: Jul. 19, 1985

Related U.S. Application Data

[63] Continuation-in-part of Ser. No. 657,356, Oct. 3, 1984, abandoned.

[51] Int. Cl.⁴ .............................. A61F 3/00; A61F 5/00
[52] U.S. Cl. ........................................................ 128/80 C
[58] Field of Search ............... 128/80 C, 80 F, 80 R, 128/88, 165; 2/22-24

[56] References Cited

U.S. PATENT DOCUMENTS

| | | | |
|---|---|---|---|
| 2,467,907 | 4/1949 | Peckham | 128/80 C |
| 2,654,365 | 10/1953 | Whitaker | 128/80 F |
| 3,055,359 | 9/1962 | Palmer | 128/80 F |
| 3,350,719 | 11/1967 | McClure, Jr. | 128/80 R X |
| 3,786,804 | 1/1974 | Lewis | 128/80 C |
| 3,817,244 | 6/1974 | Taylor | 128/80 C |
| 3,831,467 | 8/1974 | Moore | 128/80 C |
| 4,013,070 | 3/1977 | Harroff | 128/80 C |
| 4,097,932 | 7/1978 | Lacey | 128/80 F X |
| 4,183,099 | 1/1980 | Lacey | 128/80 F X |
| 4,245,629 | 1/1981 | Cummins | 2/22 X |
| 4,249,524 | 2/1981 | Anderson | 128/88 X |
| 4,361,142 | 11/1982 | Lewis et al. | 128/88 X |
| 4,370,978 | 2/1983 | Palumbo | 128/80 C |
| 4,503,846 | 3/1985 | Martin | 128/88 X |
| 4,506,661 | 3/1985 | Foster | 128/88 X |
| 4,524,764 | 6/1985 | Miller et al. | 128/88 X |
| 4,556,053 | 12/1985 | Irons | 128/88 X |

Primary Examiner—Clifford D. Crowder
Attorney, Agent, or Firm—Albert L. Gabriel

[57] ABSTRACT

A bowed leaf spring hinge structure is supported on pads attached to the thigh and shin of the wearer and is spaced laterally from the lateral side of the knee to protect the knee of an athlete against injury from lateral forces and impacts such as are likely to occur in football. The bowed leaf spring hinge structure absorbs such forces and impacts and redistributes them at locations spaced substantially above and below the knee proximate the strong bones of the leg. In one form of the invention, and anti-migration strap engages the outwardly flaring calf immediately below the knee to prevent the device from sliding downwardly on the leg.

17 Claims, 12 Drawing Figures

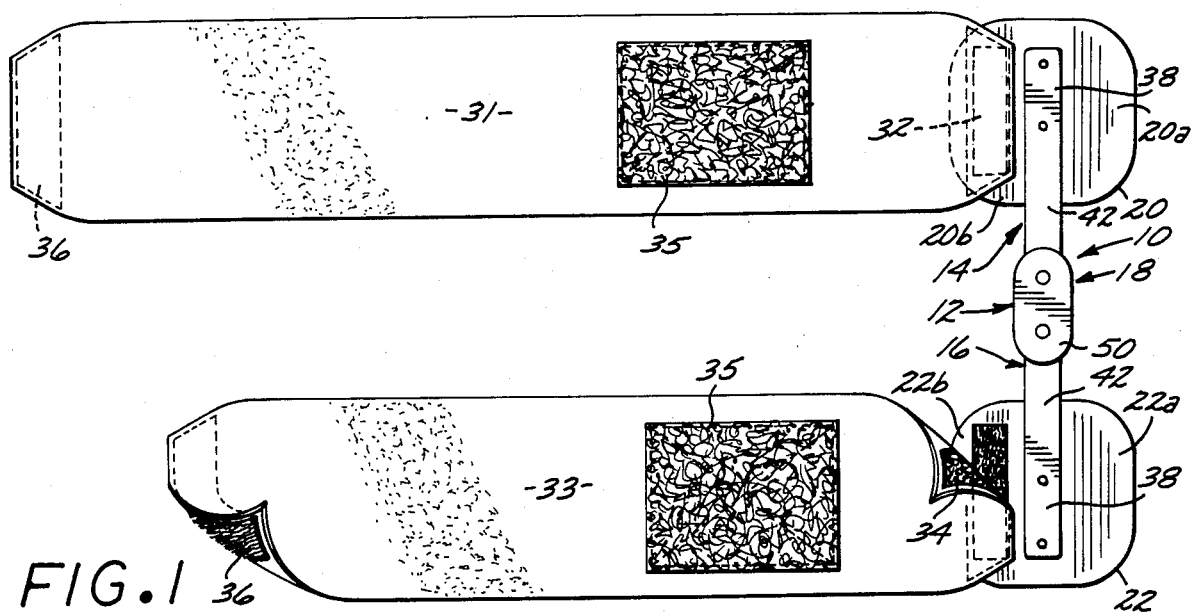
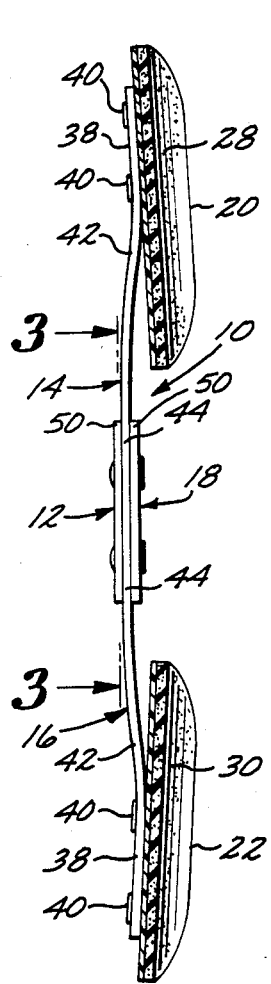
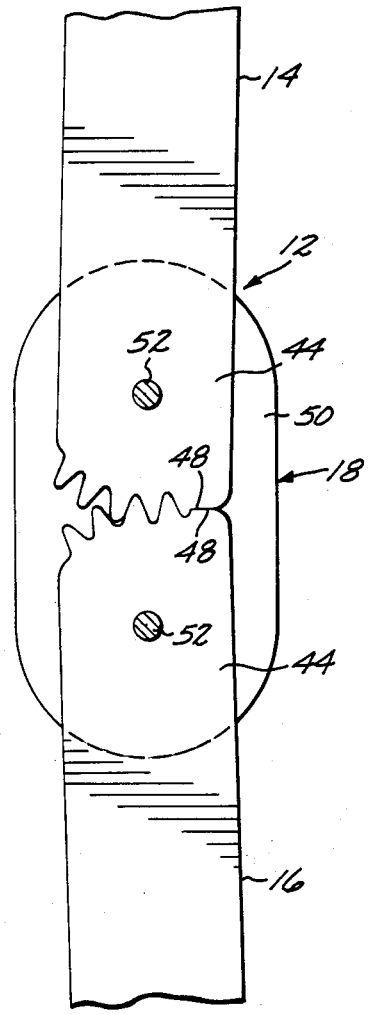
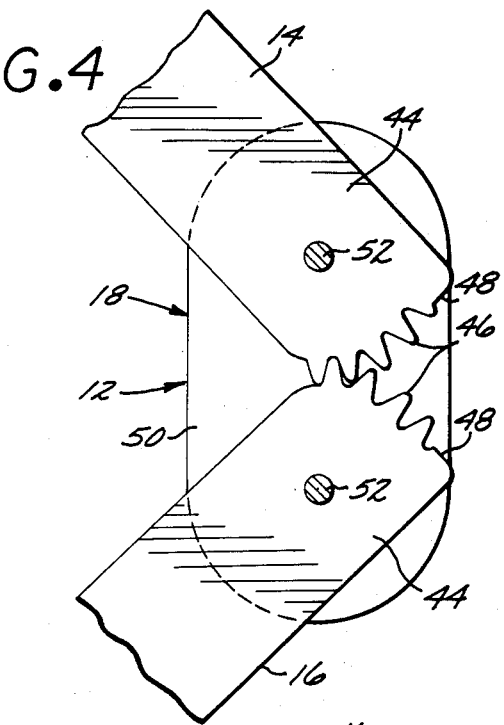
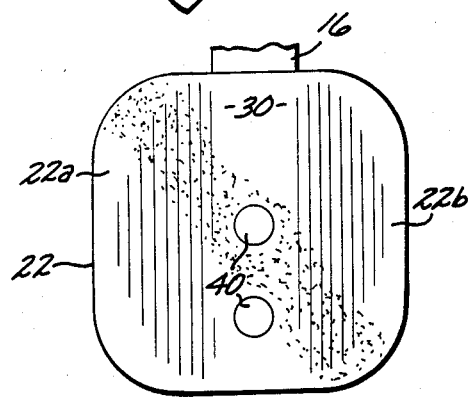

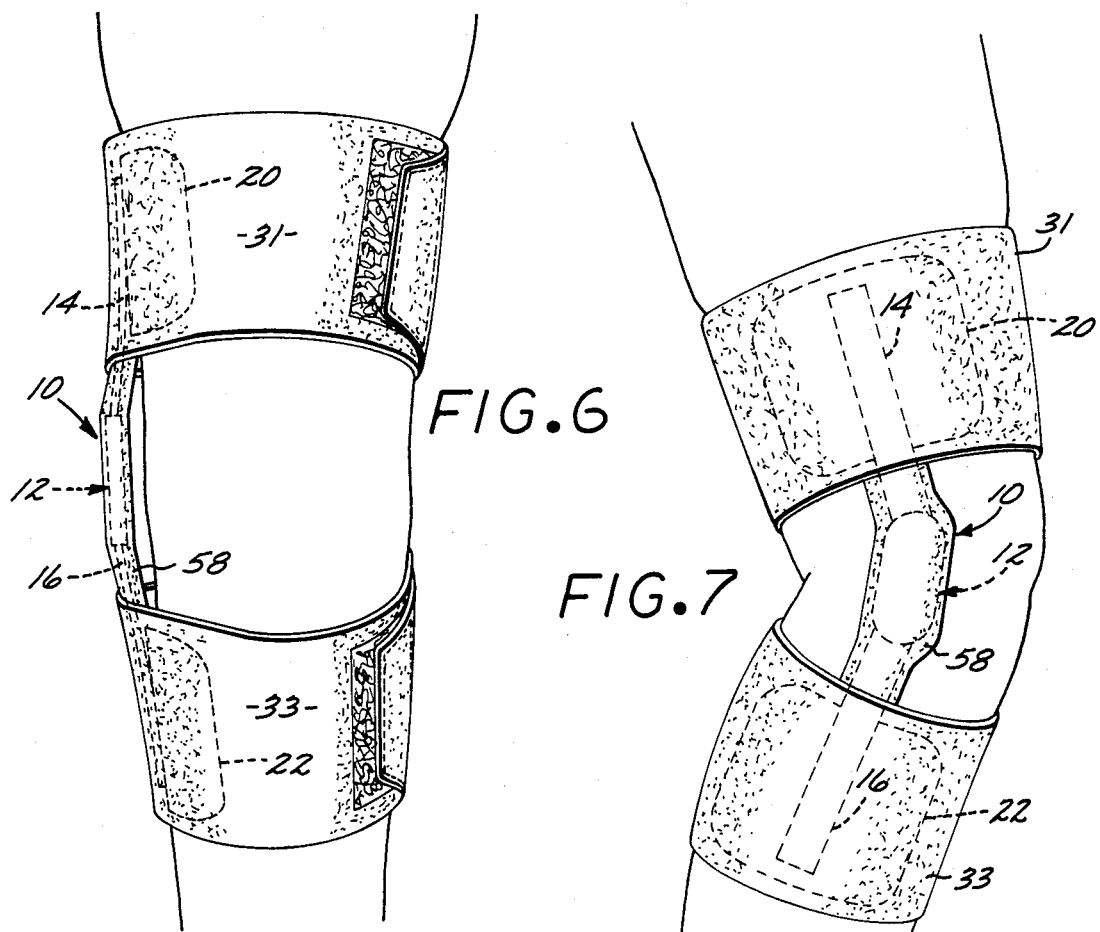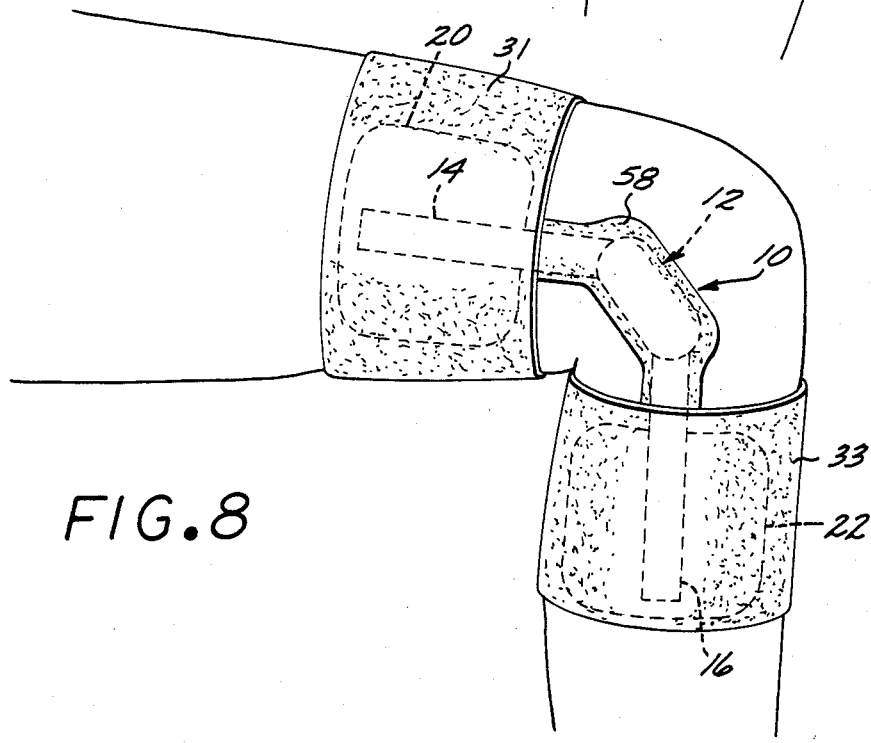

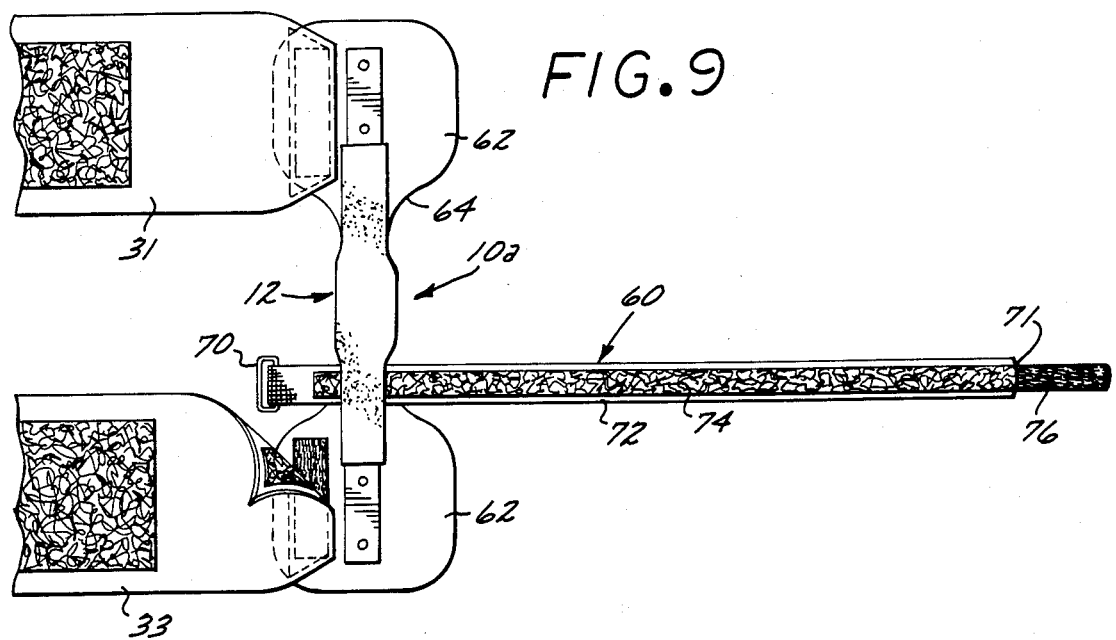
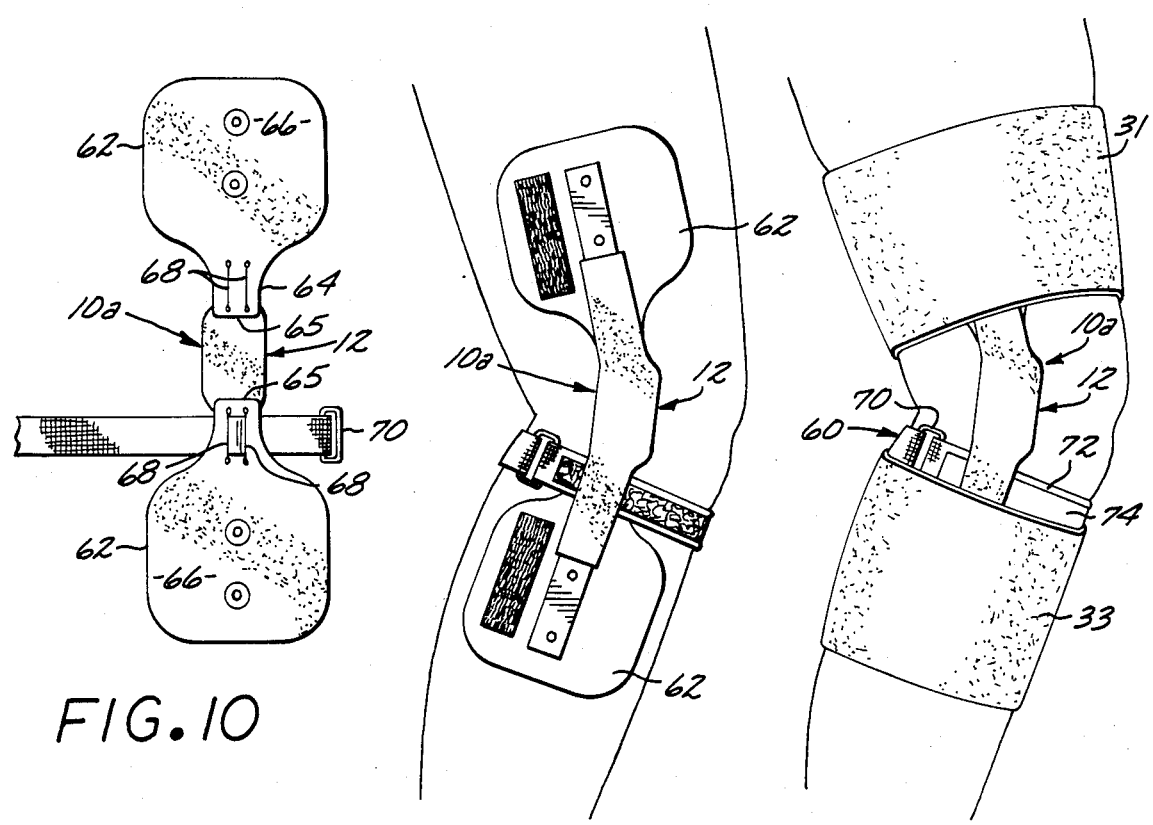

ATHLETIC KNEE PROTECTOR WITH BOWED LEAF SPRING STRUCTURE

RELATED APPLICATION

This is a continuation-in-part of our co-pending application Ser. No. 06/657,356 filed Oct. 3, 1984 for ATHLETIC KNEE PROTECTOR, now abandoned.

BACKGROUND OF THE INVENTION

1. Field of the Invention

The present invention relates to orthopedic devices for protecting the human knee, and it relates more particularly to an orthopedic device adapted to protect the knee against injury from lateral forces and impacts which may occur during sports activities.

2. Description of the Prior Art

There is widespread need for knee protection apparatus capable of absorbing forces or impacts directed toward the lateral side of the knee and redistributing such forces or impacts along the leg so as to protect a previously injured knee from further injury. A typical circumstance where such knee protection equipment would be desirable is during a game of football, where for example the person with a previously injured leg has that leg planted and another player puts a shoulder pad into the lateral side of the leg.

Applicants are aware of only two prior art protective devices directed to this specific problem, and neither of these devices has proven sufficiently satisfactory to come into widespread use. These two prior art devices are made in accordance with disclosures in U.S. Pat. No. 4,249,524 to Anderson and U.S. Pat. No. 3,528,412 to McDavid. The Anderson device consists of arms adapted to be attached to the lateral side of the thigh and calf, respectively, either by tape or neoprene wrap held with Velcro. The proximal or near ends of the arms are pivotally connected to opposite ends of a rigid metal bridge, the purpose of the device being to receive lateral forces at the bridge instead of such forces being applied directly to the knee, and to distribute such lateral forces to the femur and tibia. The Anderson device is intended to be used by football players, but it has problems such that football players in fast running positions, such as running backs, ends and the like, will not wear it. One problem is that the Anderson device has single-overlap pivots which must be fairly tight for stability, resulting in too much friction during running and hence impairment of full running freedom. Another problem with the Anderson device is that lateral force against the bridge tends to be applied to the leg primarily directly under the regions of the pivots, which is still fairly well localized at regions close to the knee, and not distributed well along the lengths of the arms to which the bridge is pivoted. A further problem with the Anderson device is that although it is biaxially pivotal, the movements at the two pivots are completely independent of each other, so that just one or just the other of the pivotal connections may move, which may cause a slippage. Also, the pivots are too far apart to simulate the hinging action of the human knee.

The device of the McDavid patent is essentially the same as the Anderson device except it has only a single single-overlap pivot located generally proximate the knee. The McDavid device has the same two principal problems as the Anderson device, namely, the single-overlap pivot needs to be fairly tight for stability, resulting in an undesirably large amount of friction during running, and lateral forces against the raised pivot tend to be applied to the leg at localized regions close to the knee and not distributed well along the lengths of the pivoted arms strapped to the thigh and calf.

Applicants are aware of a number of other prior patents directed to knee braces for protecting or supporting or limiting the motion of injured knees, but are not aware of any devices other than the Anderson and McDavid devices manufactured for the purpose of protecting the knee from lateral forces or impacts. Two of these patents, Erichsen U.S. Pat. No. 4,381,768 and Lerman U.S. Pat. No. 4,372,298 are relevant to the present invention because of biaxial, geared hinge structures similar to the geared hinge structure employed in applicants' invention. Stops are provided on the Lerman gears to limit the travel in both directions. However, neither the Erichsen or Lerman devices would be usable to absorb and redistribute lateral forces or impacts. Thus, in both of these patents, the hinged arms are described as being rigid. In Erichsen, the hinge appears to be right against the side of the knee so that lateral forces or impacts would be directly transmitted to the knee, and in Lerman, pads are attached to the hinges on opposite sides of the knee, so that lateral forces or impacts against the hinge on the lateral side of the knee would be transmitted through the respective pad directly to the knee.

Cummins U.S. Pat. No. 4,245,629 states that one of the purposes of the disclosed device is for absorbing and spreading an external blow, and Cummins is also of interest because it discloses a biaxial-type hinge structure, although it is not geared. This is a double overlap-type hinge with three tongues, described as being rigid, extending from each side of the hinge and independently pivoted in the hinge. The Cummins device does not appear to space the hinge structure from the knee, and it appears that lateral forces or impacts against the hinge would be applied directly to the knee joint or through the rigid tongues to localized regions of the leg very close to the knee.

McClure, Jr. U.S. Pat. No. 3,350,719 discloses substantially flat upper and lower brace bars that appear to be rigid, connected at a biaxial hinge. Lateral forces or impacts would either be applied through the hinge directly to the knee or through the brace bars to localized regions close to the knee.

Peckham U.S. Pat. No. 3,194,233 discloses lateral and medial leaf-type springs which bow outwardly. There is no means disclosed in this Peckham patent for spreading force to the femur and tibia at substantial spacings from the knee, and sponge pads are compressed against opposite sides of the knee joint by knee-encircling members which would cause impacts to be transmitted directly proximate the knee joint. Another Peckham U.S. Pat. No. 2,467,907 also discloses bowed springs, but so arranged that impacts would be applied directly to the knee joint. Schulman U.S. Pat. No. 3,074,400 also discloses springs in a kneecap brace, but these are not hingedly connected.

Patents such as Whitehead U.S. Pat. No. 3,898,697 and Buring U.S. Pat. No. 4,409,689 are exemplary of a number of patents which disclose shell-like forms fitting over portions of the upper and lower leg adjacent to the knee.

Applicants are aware of no prior art patent or device wherein leaf spring members are hinged together by means of a hinge substantially spaced laterally from the knee joint, and respectively rigidly connected to generally rigid thigh and shin shells at locations remote from the knee joint so as to absorb forces and impacts directed toward the lateral side of the knee and distribute such forces and impacts in a cushioned manner at locations spaced substantially from the knee and in regions of strong bones of the leg.

A problem with any knee brace is that it has a tendency to slide or migrate downwardly on the leg. This causes the hinge structure of the brace to shift out of registry with the knee joint, increasing the amount of effort required to bend the leg at the knee, and thereby generally defeating the purpose of the brace. Once downward migration commences, the strap means above the knee that is usually engaged about the thigh will rapidly loosen because of the downward and inward taper of the thigh, further impairing the utility of the device. Because of the large amount of motion at the knee joint, this downward migration problem is, in general, more serious for athletic knee protectors than for knee braces used in a less active or more sedentary way.

While a variety of calf attachment straps is provided on most knee braces as seen in the various prior art patents cited above, prior to the present invention none has been suitable for positively preventing downward migration of a knee brace, and particularly the downward migration of an athletic knee protector for protecting the knee against lateral blows. The prior art calf attachment straps have been, in general, spaced too far down below the knee joint to gain a satisfactory purchase against the initial and greatest flare of the calf immediately below the knee joint so as to provide a positive lock against downward migration. The devices disclosed in the Anderson U.S. Pat. No. 4,249,524 and McDavid U.S. Pat. No. 3,528,412 are athletic knee protector devices for protecting the knee from lateral blows, but they fall into the general category of knee braces which have calf attachment straps that are too low on the calf to prevent downward migration of the devices on the leg. The Erichsen U.S. Pat. No. 4,381,768 referred to above has a pair of straps 40 and 50 attached to the device close to the knee joint, but these straps cross over behind the knee so as to preclude engagement against the outwardly and downwardly flaring part of the calf. The knee brace disclosed in the Lerman U.S. Pat. No. 4,372,298 referred to above has a pair of straps 96 and 98 close to the knee joint, but these hold condyle pads in contact with the sides of the knee so that these straps are at the knee joint and could not engage against the flaring part of the calf. These straps 96 and 98 are elastic, which would further preclude their use as a positive stop against downward migration of the brace.

SUMMARY OF THE INVENTION

In view of these and other problems in the art, it is a general object of the present invention to provide an athletic knee protector capable of receiving and absorbing lateral forces and impacts that otherwise would be applied to the lateral side of a knee, and redistributing such forces and impacts at locations spaced substantially from the knee and in regions of strong bones of the leg.

Another general object of the invention is to provide an athletic knee protector capable of receiving and absorbing lateral forces and impacts that otherwise would be applied directly to the knee, and redistributing such forces and impacts at regions of the leg spaced substantially from the knee in such a way that the forces and impacts are, in effect, distributed generally over the whole leg as opposed to just on the point of the blow or closely adjacent to the knee.

Another object of the invention is to provide an athletic knee protector which utilizes a novel bowed leaf spring hinge structure connected at its ends to generally rigid thigh and shin pads, the bowed leaf spring hinge structure being capable of absorbing forces and impacts directed toward the lateral side of the knee and distributing such forces and impacts in a cushioned manner through the pads to the thigh and shin at locations remote from the actual knee joint.

It is another object of the invention to provide a bowed leaf spring atheletic knee protector capable of receiving shocks or impacts and spreading these out at locations on the leg remote from the knee joint, and also spreading out the time of application of such blows or impacts so as to greatly reduce the shock characteristics thereof.

A further object of the invention is to provide an athletic knee protector embodying a bowed leaf spring hinge structure covered by a foam elastomer sleeve or sheath which protects from injury another person who may impact the spring-hinge structure, and also cooperates with the leaf spring structure in extending the time of application of any impact to the wearer of the device A still further object of the invention is to provide an athletic knee protector of the character described which embodies a biaxial, geared hinge that closely follows the hinge action of the human knee and has minimal frictional resistance to its hinging action, whereby full, free running movement is achievable by an athlete wearing the device, so that athletes such as football running backs are able to wear the device without their movements being materially impeded.

Another object of the invention is to provide, particularly in an athletic knee protector but also in knee braces in general, an anti-migration strap device which engages against the initial flare of the calf immediately below the knee joint so as to positively stop the athletic knee protector or other knee brace against downward migration on the leg, and thereby maintain the hinge structure of the athletic knee protector or other knee brace in registry with the knee joint, even despite large amounts of movement associated with athletics.

The athletic knee protector of the present invention comprises a pair of leaf springs, preferably made of aluminum for lightness in weight, one of which is an upper leaf spring rigidly connected to a generally rigid thigh load distribution pad, and the other of which is a lower leaf spring rigidly connected to a generally rigid shin pad. The other ends of the two leaf springs are pivotally connected between a pair of spaced hinge plates, also preferably of aluminum, in a double-overlap or sandwich hinge construction, with the ends of the leaf springs having arcuate arrays of meshed gear teeth thereon which cause the leaf springs to pivot cooperatively in such a way as to closely resemble the hinge action of the human knee.

The leaf springs are long and are attached to the load distribution pads at regions spaced a considerable distance above and below the knee so that lateral stresses or impacts applied to the actual hinge proximate the knee are distributed along the leg at substantial distances from the knee. The springs bow outwardly to place the majority of the lengths of the springs as well as the actual hinge at a substantial spacing from the knee, and there is no intervening material between the hinge and the knee so that substantially all of the impacting or other lateral force is spread out at locations a considerable distance from the knee, and the leaf springs are free to flex under the stresses of impacts and thereby soften the blows as they are applied to the regions remote from the knee.

The double-overlap or sandwich-type hinge construction has sufficient lateral stability to enable the pivoted end portions of the leaf springs to be freely pivoted between the hinge plates while at the same time the hinge is enabled to effectively rigidly connect the pivoted ends of the two springs relative to each other in the lateral direction, so that the overall bowed leaf spring structure including the hinge acts effectively as a single long bow-shaped spring at its various hinged positions. A pair of positive stop shoulders on the hinged ends of the leaf springs lock the springs against further movement at a slightly extended position of the knee so as to prevent hyperextension.

Foam elastomer linings are provided on the inner surfaces of the load distribution pads to cushion the engagement between the pads and the skin. Wrap-around elastomer attachment sheets are attachable by Velcro to the outer surfaces of the pads and are adapted to be stretched around the thigh and calf and their respective pads and secured to themselves by Velcro. A foam elastomer sleeve or sheath is placed over the hinge and the bowed portions of the leaf springs to protect from injury another person who might impact against these structures, and this also serves to cooperate with the leaf springs in softening the application of impacts to the leg.

The foam elastomer linings on the inner surfaces of the load distribution pads provide an anti-slip engagement with the skin which gives some control against downward slipping or migration of the athletic knee protector of the invention. However, to provide positive assurance against downward migration, the invention also includes an anti-migration strap which is flexible but nonelastic, and which is attachable to the shin pad of the device immediately below the hinge of the device at a location enabling the anti-migration strap to be engaged about the calf immediately below the knee where the calf has its initial and greatest flare, so as to positively stop the athletic knee protector against downward migration on the leg. This anti-migration strap of the invention is also attachable to other types of hinged knee braces immediately below the hinge structures and engageable about the uppermost part of the calf to prevent downward migration of the braces.

BRIEF DESCRIPTION OF THE DRAWINGS

These and other objects of the invention will become more apparent in view of the following description taken in conjunction with the drawings, wherein:

FIG. 1 is a plan view of a fully assembled athletic knee protector according to the invention, laid out generally flat with the outer surfaces of the device facing upwardly;

FIG. 2 is a vertical section taken on the line 2—2 of FIG. 1;

FIG. 3 is a sectional view, partly in elevation, taken on the line 3—3 in FIG. 2 greatly enlarged from FIGS. 1 and 2, but with the parts shown in approximately the same size as an actual device made in accordance with the invention, the leaf spring hinges being fully extended to the stop position in FIG. 3;

FIG. 4 is a sectional view, partly in elevation, similar to FIG. 3 but with the leaf springs pivoted to a flexion angle of slightly more than 90°;

FIG. 5 is a plan view illustrating the cushioned inner surface of one of the load distribution pads;

FIG. 6 is a fragmentary elevational view, with covered parts shown in dashed lines, showing the athletic knee protector of the invention mounted on the leg of a wearer, with the knee and the athletic knee protector of the invention at approximately 0° of flexion;

FIG. 7 is a view similar to FIG. 6, but with the knee and the athletic knee protector of the invention at approximately 30° of flexion;

FIG. 8 is a view similar to FIGS. 6 and 7, but with the knee and the athletic knee protector of the invention at approximately 90° of flexion;

FIG. 9 is a fragmentary plan view similar to FIG. 1 of a fully assembled athletic knee protector which is modified to include an anti-migration strap, the athletic knee protector being laid out generally flat with the outer surfaces of the device facing upwardly;

FIG. 10 is a fragmentary plan view of the device shown in FIG. 9 with the elastomer attachment sheets removed, the device being laid out flat with the inner surfaces of the device facing upwardly;

FIG. 11 is a side elevational view illustrating the athletic knee protector of FIGS. 9 and 10 operatively positioned on the leg of a wearer with the anti-migration strap engaged about the calf, the device being illustrated without the elastomer attachment sheets which secure the load distribution pads to the thigh and shin; and FIG. 12 is a view similar to FIG. 11, but with the thigh and shin load distribution pads attached to the thigh and shin by means of the elongated elastomer attachment sheets.

DETAILED DESCRIPTION

Referring to the drawings, and at first to FIGS. 1–8, the athletic knee protector of the present invention is generally designated 10, and is adapted to be attached to the thigh and shin of the user in the manner shown in FIGS. 6, 7 and 8 to present a bowed leaf spring hinge structure generally designated 12 in spaced relationship to the lateral or outer side of the knee to protect the knee of an athlete against injury from lateral forces and impacts such as are likely to occur in football and soccer. The knee protector 10 of the invention also provides support for a previously injured knee. Despite such protection and support afforded by the athletic knee protector 10 of the invention, its unique leaf spring hinge structure 12 enables full, free running movement to be achieved by an athlete wearing the device, so that athletes such as football running backs who heretofore would not wear devices of this general type find the present invention does not impede their movements, and are accordingly willing to wear the athletic knee protector 10 of the invention.

The knee protector 10 as illustrated in the drawings is arranged to protect the right knee. The same knee protector 10 is used inverted for the left knee so that its parts are reversed or arranged as a mirror image relative to those of the knee protector 10 as shown in the drawings.

The overall construction of the athletic knee protector 10 of the invention is best seen in FIG. 1, wherein the fully assembled device is laid out generally flat with the outer surfaces of the device facing upwardly. The leaf spring hinge structure 12 consists of upper and lower leaf spring members 14 and 16 hingedly connected by means of a biaxial or bicentric hinge 18. The leaf spring hinge structure 12 will be described hereinafter in detail in connection with FIGS. 2-4 of the drawings. An upper end portion of the upper leaf spring member 14 is rigidly attached to an upper portion of a thigh load distribution pad 20; similarly, a lower end portion of the lower leaf spring member 16 is rigidly attached to a lower portion of a shin load distribution pad 22.

The load distribution pads 20 and 22 are made of substantially rigid sheet plastic material such as a high density polyethylene which has sufficient rigidity or stiffness when operatively mounted on the leg to distribute a load or impact over a considerable area of the leg. The load distribution pads 20 and 22 are contoured so as to substantially conform with the configurations of the lateral side of the thigh and shin when operatively mounted on the leg. Referring to FIG. 1, each of the load distribution pads 20 and 22 has a respective anterior portion 20a and 22a and posterior portion 20b and 22b.

Foam elastomer linings 28 and 30, which are at least coextensive with the pads 20 and 22 and which may be made of foam neoprene, are bonded to the inner surfaces of the respective thigh and shin pads 20 and 22 to serve the multiple functions of providing soft cushioning under the generally hard pads and providing anti-slip engagement with the skin. An elongated elastomer attachment sheet 31, which may or may not be foam elastomer, is releasably attachable to the outer surface of the posterior portion 20b of pad 20 by Velcro means 32 and extends posteriorly of such attachment; and a similar, somewhat shorter elastomer attachment sheet 33 is releasably attachable to the outer surface of the posterior portion 22b of pad 22 by Velcro means 34 and extends posteriorly of such attachment.

An outwardly-facing Velcro pad 35 is mounted on each of the elastomer sheets 31 and 33 adjacent to the respective pads 20 and 22, and a complementary inwardly-facing Velcro hook strip 36 is mounted on each of the elastomer sheets 31 and 33 proximate its free end.

The athletic knee protector 10 is mounted on the leg by placing the foam linings 28 and 30 of respective load distribution pads 20 and 22 against the lateral sides of the thigh and shin, respectively, then wrapping the attachment sheets 31 and 33 posteriorly around the thigh and calf, respectively, and then anteriorly medially and then over the exposed surfaces of the respective load distribution pads 20 and 22 and the attached end portions of the respective leaf spring members 14 and 16, and then attaching the Velcro strips 36 to the respective Velcro pads 35. This wrap-around attachment is made sufficiently tightly to stretch the elastomer attachment wraps 31 and 33 so as to firmly secure the cushioned pads 20 and 22 to the thigh and shin, respectively. In this operative, mounted location of the athletic knee protector 10, the foam elastomer linings 28 and 30 underlying the respective pads 20 and 22 not only protect skin and flesh from the generally rigid shells, but also provide an anti-slip engagement with the skin which gives some control against downward migration of the knee protector 10.

An alternative means for mounting the pads 20 and 22 on the thigh and shin, respectively, is to tape each of the pads 20 and 22 into position. If this is to be the case, the attachment wraps 31 and 33 would be removed from the knee protector 10 by disengagement of the respective Velcro means 32 and 34.

Reference will now be made particularly to FIGS. 2, 3 and 4 which show the details of construction of the leaf spring hinge structure 12. Each of the leaf springs 14 and 16 includes a flat attachment end portion 38 rigidly attached to the respective pad 20 or 22, preferably by means of a plurality of fasteners 40 such as screws or rivets longitudinally spaced on the leaf spring attachment portion 38. Moving toward the hinge 18, each of the leaf springs 14 and 16 next has a laterally outwardly-bowed portion 42, and this bowed portion 42 terminates in a flat hinge portion 44. At the end of each flat hinge portion 44 is an arcuate array 46 of gear teeth which end in a stop shoulder 48 proximate the anterior edge of each leaf spring 14 and 16. The flat hinge portions 44 of leaf springs 14 and 16 are pivotally engaged between a pair of hinge plates 50 on respective pins 52 which may be rivets as shown. The gear teeth 46 on the hinged ends of leaf springs 14 and 16 are in meshing engagement which causes the springs 14 and 16 to pivot cooperatively and not independently relative to the hinge plates 50, and such cooperative pivoting of the springs 14 and 16 about the spaced axes of the pivot pins 52 causes the biaxial or bicentric hinge 18 to closely simulate the hinge action of the human knee. By this means, resistance of the hinge 18 to free pivoting or hinging movement of the knee is minimized. The leaf springs 14 and 16 and the hinge plates 50 are preferably made of aluminum for lightness in weight.

The double overlap or sandwich construction of the leaf springs 14 and 16 between the pair of hinge plates 50 is so stable in the transverse or lateral direction that the pivots can be quite free and do not need to be tight as in the single overlap pivot arrangements used in prior art devices intended for this same purpose of protection against injury from lateral forces, and such freedom of movement cooperates in minimizing resistance to knee movement, and hence in enabling full, free running movement to be achieved by an athlete wearing the device.

The leaf springs 14 and 16 are relatively long, and by having the upper leaf spring 14 attached to an upper portion of the thigh load distribution pad 20 and the lower leaf spring 16 attached to a lower portion of the shin load distribution pad 22, the regions of attachment of the springs 14 and 16 are, when the device 10 is worn, located respectively at a considerable distance above and below the actual knee joint adjacent to the strong bones of the leg, the femur and tibia, respectively. The stability of the double overlap, biaxial hinge 18, coupled with the long spring arms 14 and 16 attached to the pads 18 and 20, respectively, at considerable spacings from the knee joint, enable the device 10 to absorb forces and impacts directed toward the lateral side of the knee and distribute such forces and impacts in a cushioned manner at locations spaced substantially from the knee and in regions of strong bones of the leg. The generally rigid nature of the load distribution pads 20 and 22 causes such forces and impacts to be spread out over the substantial areas of the pads 20 and 22, and the spring action of the leaf springs 14 and 16 spreads the impact out not only in area, but also in time. The athletic knee protector 10 of the invention has the effect of distributing lateral forces generally over the whole leg as opposed to just on the point of the blow or closely adjacent to the knee, as with prior art devices which attempted to accomplish what the present invention in fact accomplishes.

The stop shoulders 48 come into engagement with each other as shown in FIG. 3 when the leaf springs 14 and 16 are extended slightly beyond axial alignment, which corresponds to a slight amount of extension of the knee. This prevents any further extension of the leaf springs 14 and 16, and thereby prevents any possibility of hyperextension of the knee. The hinge 18 allows pivoting from such slightly extended, stopped position through whatever angle of flexion may be necessary for any sport, as for example the slightly more than 90° of flexion illustrated in FIG. 4. FIGS. 6, 7 and 8 illustrate the athletic knee protector 10 of the invention operatively located, with the knee in three different conditions of flexion. FIG. 6 illustrates the knee protector 10 with the knee at approximately 0° of flexion, or possibly slightly extended with the device substantially in the hinged condition of FIG. 3; FIG. 7 illustrates the knee protector 10 with the knee, and hence also the leaf spring hinge structure 12, at approximately 30° of flexion; and FIG. 8 illustrates the knee, and hence the leaf spring hinge structure 12, at approximately 90° of flexion.

It will be seen in FIGS. 6, 7 and 8 that the hinge 18 and flat hinge portions 44 and outwardly-bowed portions 42 of leaf springs 14 and 16 are covered by a foam elastomer sleeve or sheath 58 which is installed prior to attachment of at least one of the leaf spring end portions 38 to its respective load distribution pad 20 or 22. This foam elastomer sleeve 58 may be made of foam neoprene, and serves the dual functions of protecting another person from being injured who may impact the hinge structure 12, and also cooperates with the leaf springs 14 and 16 in extending the time of application of any impact to the load distribution pads 20 and 22 and hence to the thigh and shin.

As best seen in FIGS. 2 and 6, there is substantial spacing between the hinge 18 and the outwardly-bowed portions 42 of both of the leaf springs 14 and 16 on the one hand and the load distribution pads 20 and 22 on the other hand. This is essential for effective operation of the athletic knee protector 10 in protecting the knee of the wearer from lateral forces and impacts, as the filling of this void with any material, even a foam plastic material, would enable at least part of any lateral force or impact to be transmitted directly to the knee and would correspondingly diminish the effectiveness of the knee protector 10. With the complete void in this region, the knee protector 10 of the invention is enabled to substantially completely protect the knee from lateral forces or impacts.

Since the athletic knee protector 10 of the invention requires the leaf spring hinge structure 12 on only the lateral side thereof and requires no hinge structure on the medial side of the device, this leaves the medial side substantially unobstructed for freedom in athletic movement.

FIGS. 9-12 illustrate a modified form of athletic knee protector according to the invention, this form being generally designated 10a. The athletic knee protector 10a of FIGS. 9-12 is identical to the athletic knee protector 10 of FIGS. 1-8 except for the addition an anti-migration strap 60 and modified load distribution pads 62 which each have an integral tongue 64 extending in the general longitudinal direction of the knee protector 10a in the proximal direction toward the knee as best seen in FIG. 10. With the athletic knee protector 10a mounted on a leg of a user, the proximal inner, free ends 65 of tongues 4 extend close to but just short of the actual knee joint. Foam elastomer linings 66 cover the inner surfaces of the load distribution pads 62, the foam elastomer linings 66 being coextensive with the respective load distribution pads 62 so as to cover not only the wide portions of the pads 62 but also the tongues 64.

A pair of longitudinally arranged, parallel strap slots 68 extends through each of the tongues 64, including the foam lining portions 66. By thus having a strap tongue 64 with strap-receiving slots 68 on each of the load distribution pads 62, the athletic knee protector 10a is adapted for operative mounting on the lateral side of either leg, with the anti-migration strap 60 engaged through the strap slots 68 of the tongue 64 which is below the hinge structure 12 for that particular leg. The athletic knee protector 10a as illustrated in FIGS. 9-12 is adapted for use on the lateral side of the right leg. The same athletic knee protector 10a is adaptable for mounting on the lateral side of the left leg by simply inverting the knee protector 10a so that the hinge structure 12 is in the proper direction for flexion with the leg, and when thus inverted for use on the left leg, the anti-migration strap 60 must be moved from the location illustrated in FIGS. 9-12 and engaged through the strap slots 68 of the other tongue 64.

The anti-migration strap 60 is made of a material that is flexible but substantially nonstretchable, as for example a heavy woven nylon belt-type material. A rigid loop 70, preferably of metal, is secured to one end of strap 60 and is adapted to have the other, free end 71 of strap 60 engaged therethrough. The outer surface 72 of strap 60 has a Velcro pad strip 74 extending along most of its length, and an outwardly facing Velcro hook strip 76 extends longitudinally from the free end 71 of strap 60. When the strap 60 is engaged around the upper calf of the wearer, the Velcro hook strip 76 and free end 71 of strap 60 are engaged through the strap loop 70 and doubled back over the outside of strap 60, the Velcro hook strip 76 then being attached to the outwardly exposed Velcro pad strip 74 with the strap snugly secured about the calf where the calf flares outwardly immediately below the knee joint. This provides a positive interlock between the anti-migration strap 60 and the flare of the calf which prevents any downward migration of the athletic knee protector 10a on the leg, and retains the hinge structure 12 substantially in registry with the knee joint despite heavy athletic use, and even despite any tendency the knee protector might otherwise have to slip because of the presence of perspiration between the foam elastomer linings 66 and the leg.

It is to be noted that the anti-migration strap 60 is attached to a tongue 64 of one of the load distribution pads 62 rather than being attached to or engaged over the leaf-spring hinge structure 12. This avoids any tendency to compress the leaf-spring hinge structure 12 toward the knee joint, leaving the hinge structure 12 spaced outwardly from the knee as seen in FIG. 6 so as to be effective in absorbing lateral forces and impacts without transmitting them directly to the knee.

In the appended claims, the term "knee protection device" is intended to refer not only to an athletic knee protector but also to other types of hinged knee braces.

While the instant invention has been described with regard to particular embodiments, modifications may readily be made by those skilled in the art, and it is intended that the claims cover any such modifications which fall within the spirit and scope of the invention.

We claim:

1. An athletic knee protector for protecting the knee of a wearer from forces and impacts directed toward the lateral side of a knee, which comprises:

first and second pad means attachable respectively to the thigh and shin of the wearer;

an upper leaf spring connected to said thigh pad means at a location spaced substantially above the knee and extending downwardly generally parallel to the thigh to a lower end portion located generally laterally of the knee;

a lower leaf-spring having a lower end portion connected to said shin pad means and extending upwardly generally parallel to the shin to an upper end portion located generally laterally of the knee; and hinge means hingedly connecting said lower end portion of said upper leaf spring and said upper portion of said lower leaf spring, said hinge means providing substantially free anterior/posterior pivotal movement between said leaf springs corresponding to anterior/posterior pivotal movement of the knee, but providing a substantially rigid connection between said leaf springs in the lateral/medial direction;

said leaf springs and said hinge means together defining a bowed leaf spring structure that is generally continuously bowed between said connection to said thigh pad means and said connection to said shin pad means, said leaf springs bowing laterally outwardly from their said connections to their respective said pad means so that said hinge means is substantially spaced laterally outward from the knee of the wearer;

said bowed leaf spring structure being resiliently flexible in the lateral/medial direction so as to absorb forces and impacts directed toward the lateral side of the knee, distributing such forces and impacts in a cusioned manner through said thigh and shin pads to the thigh and shin, respectively, at locations substantially spaced from the knee, and spreading out the time of application of such forces and impacts so as to reduce the shock characteristics thereof.

2. An athletic knee protector as defined in claim 1, wherein said hinge means is biaxial.

3. An athletic knee protector as defined in claim 2, wherein said hinge means comprises a pair of hinge plates disposed on opposite sides of said leaf springs, each of said leaf springs being pivotally connected to said pair of hinge plates on a respective pivot axis.

4. An athletic knee protector as defined in claim 3, wherein said leaf springs are freely pivoted between said hinge plates for minimum frictional resistance to athletic movement of the knee.

5. An athletic knee protector as defined in claim 4, wherein the hinged ends of said leaf springs have meshed arcuate arrays of gear teeth thereon for coordinated movement between said leaf springs as they pivot within said hinge plates, whereby the hinging movement between said leaf springs generally registers with the hinging movement of the knee of the wearer.

6. An athletic knee protector as defined in claim 5, wherein the hinged ends of said leaf springs have opposed stop shoulders thereon, said stop shoulders being engagable to limit the amount of pivotal extension of said leaf springs relative to each other and thereby prevent hyperextension of the knee.

7. An athletic knee protector as defined in claim 1, wherein said upper end portion of said upper leaf spring is connected to an upper portion of said thigh pad means and said lower end portion of said lower leaf spring is connected to a lower portion of said shin pad means so as to maximize the spacings of said leaf spring connections from the knee of the wearer.

8. An athletic knee protector as defined in claim 1 which comprises foam elastomer sheath means covering said hinge means and said leaf springs between the locations at which they are connected to their respective said shell means.

9. An athletic knee protector as defined in claim 1 which comprises foam elastomer lining means substantially covering the underside of each of said pad means.

10. An athletic knee protector as defined in claim 1, which comprises an elastomer attachment wrap connected to each of said pad means and adapted to wrap around the leg and the respective pad means, and Velcro means on each of said attachment wraps for releasably securing the respective attachment wrap to itself.

11. An athletic knee protector as defined in claim 10, wherein said attachment wraps are releaseably connected to the respective said pad means.

12. An athletic knee protector as defined in claim 1, wherein said first and second pad means are similar in configuration such that each is attachable to either a thigh or a shin of the wearer, whereby in one orientation of the protector said first and second pad means are attachable respectively to the thigh and shin of one leg of the wearer to protect that leg, and in an inverted orientation of the protector said first and second pad means are attachable respectively to the shin and thigh of the other leg of the wearer to protect that leg.

13. An athletic knee protector as defined in claim 1 which comprises anti-migration strap means connected to said second pad means immediately below said hinge means and engageable around the outwardly flaring part of the calf of the wearer immediately below the knee so as to provide a positive stop against downward migration of the protector along the leg of the wearer.

14. An athletic knee protector as defined in claim 13, wherein said strap means comprises a strap which is flexible but substantially nonstretchable.

15. An athletic knee protector as defined in claim 13, wherein said second pad means has an integral upwardly extending tongue thereon to which said strap means is attached.

16. An athletic knee protector as defined in claim 12 which comprises anti-migration strap means selectively releaseably attachable to each of said pad means immediately adjacent to said hinge means, said strap means being adapted for selective attachment to the said pad means that is attached to the shin of the wearer and being engageable around the outwardly flaring part of the calf of the wearer immediately below the knee so as to provide a positive stop against downward migration of the protector along the leg of the wearer.

17. An athletic knee protector as defined in claim 16, wherein each of said pad means has an integral tongue thereon extending generally toward said hinge means, said strap means being selectively attachable to each of said tongues.

* * * * *